United States Patent [19]

Schmidt et al.

[11] 4,115,443
[45] Sep. 19, 1978

[54] PROCESS OF MAKING D,L-LITHIUM PANTOATE AND RESOLVING THE RACEMIC MIXTURE INTO ITS OPTICALLY ACTIVE ISOMERS

[75] Inventors: Joachim Schmidt; Christian Weigelt; Wolfgang Bamberg; Wolfgang Schneider, all of Jena, Democratic Rep. of Germany

[73] Assignee: Veb Jenapharm, Jena, Democratic Rep. of Germany

[21] Appl. No.: 670,437

[22] Filed: Mar. 25, 1976

Related U.S. Application Data

[60] Continuation of Ser. No. 540,249, Jan. 10, 1975, abandoned, which is a division of Ser. No. 407,254, Oct. 17, 1973, abandoned.

[51] Int. Cl.$^2$ .............................................. C07C 59/04
[52] U.S. Cl. .................. 562/402; 260/343.6; 562/579
[58] Field of Search ...................... 260/535 R, 343.6

[56] References Cited

U.S. PATENT DOCUMENTS

| 2,739,157 | 3/1956 | Hammond | 260/343.6 |
| 3,405,159 | 10/1968 | Kreeger | 260/465 D |

OTHER PUBLICATIONS

Organic Chemistry (An Advanced Treatise), vol. 1, 2nd Ed., pp. 254–256.

*Primary Examiner*—Paul J. Killos
*Attorney, Agent, or Firm*—Michael J. Striker

[57] ABSTRACT

A process for the resolution of optical isomers of racemic lithium pantoate by selective crystallization from a solution in methanol, ethanol, or other polar solvents, or by electrostatic separation. The optical isomers can be readily converted to optically active pantolactones which are the starting material for the preparation of optically active pantothenic acid and its salt and pantothenyl alcohol. One of the two optical isomers of each of these compounds possesses vitamin activity. The unwanted or inactive optical isomer of lithium pantoate as such is thermally stable and can be racemized by heating in the presence of a basic reacting compound at a temperature between 120 and 180° C to produce a racemic mixture which can then be subjected directly to resolution without conversion to some other derivative in accordance with the processes of the present invention to produce the desired or active optical isomer.

4 Claims, No Drawings

PROCESS OF MAKING D,L-LITHIUM PANTOATE AND RESOLVING THE RACEMIC MIXTURE INTO ITS OPTICALLY ACTIVE ISOMERS

This is a continuation of application Ser. No. 540,249, filed Jan. 10, 1975, now abandoned, which is a div. of Ser. No. 407,254, filed Oct. 17, 1973, now abandoned.

BACKGROUND OF THE INVENTION

The present invention pertains to processes for the resolution of optical isomers of lithium pantoate without the use of optically active resolving agents.

Pantolactone is used for the production of pantothenyl alcohol, pantothenic acid and its salts, such as, for example, calcium pantothenate, which possess vitamin activity and are useful as vitamins. Since such biological activity as vitamins is exhibited only by D(+) isomers, a method is required for resolving racemic mixtures of pantolactone. The resolution can be effected either with pantolactone itself or with calcium pantothenate.

Of the many conventional methods for the resolution of optical isomers, such as adsorption, distillation, use of resolving agents, enzymatic or microbiological separation, conversion to diastereoisomeric pairs of salts, selective or preferential crystallization, and electrostatic separation, the only methods that have been found heretofore to be suitable for the resolution of optical isomers of pantolactone were the use of diastereoisomeric pairs of salts or preferential crystallization of ammonium pantoate which latter method is described, for example, in U.S. Pat. No. 3,529,022. Optical isomers of calcium pantothenate can also be resolved by preferential crystallization.

For separation by formation of pairs of diastereoisomeric salts, the process consists generally either in conversion of the racemic mixture of pantolactones with a suitable optically active base, or conversion of a metal salt of the racemic mixture of pantolactone with a salt of an optically active base and a strong acid. This conversion is effected generally in an alcoholic, aqueous alcoholic, or aqueous medium. There is thus obtained a salt of an optically active isomer having a degree of purity that is dependent upon the solvent and the base used. The corresponding enantiomorphs remain in the mother liquor. The salt and the mother liquor are then separated and the salt is treated in such manner that, after addition of acid, the desired optical isomer of pantolactone is isolated and the base is recovered. The unwanted optically inactive isomer of pantolactone is racemized and the racemic mixture is again resolved to obtain the desired optical isomer.

Optically active bases that were used heretofore included naturally occurring alkaloids such as quinine and ephedrine as well as synthetic optically active compounds such as L-threo-1-(p-nitrophenyl)-2-amino-1,3-propanediol. Of the synthetic optically active compounds, $\beta$-phenylethylamine and dehydroabietylamine are also of importance.

Another method of resolving DL-pantolactones which is described in U.S. Pat. No. 2,383,524 depends upon the use of anhydrides of diacyl-D-tartaric acids, with which the pantolactone is esterified. Pyridine salts of the racemic esters are then formed and, because of their differences in solubility in benzene, the optical isomers are then separated from each other.

For separating racemic pantolactone into its optical isomers by means of preferential crystallization, the racemic mixture is converted into the corresponding ammonium salt and the differences in solubilities of the D and L-ammonium pantoates with respect to the DL-ammonium pantoate racemic mixture in various solvents is utilized for separating the two isomers. The thus-obtained D and L-ammonium pantoate are separated and are so treated that, following the addition of acid, the desired optically active pantolactone is isolated in conventional manner. DL-calcium pantoate is also susceptible to resolution by preferential crystallization in a manner similar to that used for separating racemic ammonium pantoate.

The foregoing methods have a number of disadvantages. The usefulness of the method for separating optical isomers by means of pairs of diastereoisomeric salts is limited by the bases that are required which are mostly naturally occurring alkaloids. Furthermore, because the cost of such bases is very high, it is necessary to recover the bases, which adds to the costs. Since these bases are also toxic or most highly active physiologically, this constitutes a further concomitant disadvantage. By racemization of the unwanted isomers the salt with the optically active base that is used must be cleaved into its separate components, otherwise the optically active base would also be racemized. This cleavage, combined with the further treatments that are required, represent a considerable additional expense.

By using L-threo-1-(p-nitrophenyl)-2-amino-1,3-propanediol, which is an intermediate in the production of chloramphenicol, one is necessarily dependent upon the extent of the use of that compound in the production of chloramphenicol. The same reservations that apply to naturally occurring alkaloids also apply in the case of this resolving agent.

In the case of dehydroabietylamine the required higher dilution of the mixture that is to be resolved is a disadvantage because of the increased expenses that are incurred.

The use of diacyl-D-tartaric anhydrides is limited likewise by high cost and the treatments that are required as well as by the toxic solvents that are required.

Although a number of the disadvantages of processes of using optically active bases such as, for example, the difficulty of procuring the bases, their high cost, and the high cost for subsequently recovering the bases are avoided in the process of separating the optical isomers of pantolactone by preferential crystallization of ammonium pantoate because ammonia is readily available, the process is nonetheless fraught with a number of disadvantages. When pantolactone is reacted with ammonia, for example, the amide of pantoic acid is also obtained as well as the desired ammonium pantoate together with a series of further reaction products, such as amines and amides which to a great extent unfavorably affect the subsequent selective crystallization which is a very delicate procedure that is readily disturbed by even a small proportion of such by-products. Even with great care, the production of these by-products cannot be entirely avoided. A further disadvantage of the use of ammonium pantoate for separating the optical isomers of pantolactone from each other is that the unwanted isomer cannot readily be racemized. Ammonium pantoate cannot itself directly racemize since it is converted to various of the same by-products that form when pantolactone is reacted with ammonia. For the purpose of racemization, the unwanted ammonium pantoate must first be converted to pantolactone, which is then racemized and which then must be converted back to ammonium pantoate so that the optical isomers in the racemic mixture can then be separated from each other.

The use of selective crystallization for separating the isomers of DL-calcium pantoate as an amide of pantoic acid is also fraught with disadvantages. After separation of the optically active isomers, sodium methoxide in an nonaqueous medium must be used to racemize the unwanted isomeric component of the mixture. If only a fraction of 1% of water is present, the calcium pantoate is split into pantolactone and $\beta$-alanine and, if 1% water is present, the yield is only 50% of the theoretical, so that this reaction step can also involve high costs unless the splitting of the calcium pantothenate during the racemization can be completely prevented. Another disadvantage of this selective crystallization method is that it is limited to calcium pantoate, so that, when used for the preparation of D(+)-pantothenyl alcohol, optically active pantolactone is not formed and must be prepared in a separate operation.

SUMMARY OF THE INVENTION

The object of the present invention is to provide a process for reducing substantially the cost of separating optical isomers of pantolactone, heretofore limited on one hand by the high cost of the resolving agents and on the other hand by the high cost of the processing treatments that were required.

Another object of the present invention is to provide a process for producing the optically active pantolactone in a high yield and in a high degree of purity.

The object of the present invention is accordingly to provide a process for resolving racemic pantolactone into its optical isomers without the use of optically active bases which are expensive and highly toxic resolving agents, by means of which the cost of resolving pantolactone in comparison with known processes is considerably reduced.

In accordance with the present invention, these objects are achieved by using a simple compound of racemic pantolactone, which on the one hand can be resolved either by selective crystallization or by electrostatic separation and on the other hand can be racemized and, after racemization and without further purification, the racemic mixture can be again resolved into its optical isomers.

It has been discovered that the foregoing objects can be achieved by using lithium pantoate, which can be prepared from basic lithium compounds and pantolactone in a polar solvent, preferably a lower alkanol or in water, or by metathesis of salts of pantoic acid, for example, calcium pantoate and lithium oxalate, or barium pantoate and lithium sulfate in an aqueous medium. Basic lithium compounds which can be used for the preparation of lithium pantoate are lithium carbonate and lithium hydroxide. Lithium pantoate in the presence of a polar solvent, preferably a lower alkanol, can be resolved into its optical isomers in accordance with conventional selective crystallization procedures, and the desired optically active form of lithium pantoate can then be converted in accordance with conventional methods into optically active pantolactone. A particular advantage of the process of the present invention is that it can be used to purify crude pantolactone by converting the pantolactone into the DL-lithium pantoate, which is thermally stable at the temperatures required and has a high coefficient of solubility with increasing temperature and which accordingly can be easily crystallized from saturated solutions thereof.

It was further discovered that the unwanted optically active form of lithium pantoate that is obtained as an accompanying by-product in the polar solvent, such as a lower alkanol, either dissolved or suspended therein, can be racemized to DL-lithium pantoate at a temperature between 120° and 180° C, in the presence of an alkaline catalyst, for example aliphatic amines, alkali-metal hydroxides or alkali-metal carbonates. The racemic lithium pantoate thus obtained can without further treatment or purification be subjected directly to resolution by selective crystallization.

The racemic mixture of lithium pantoate crystals obtained by crystallization from polar solvents can also be separated into its optical isomers in an electrostatic separator in accordance with conventional methods, as illustrated in Example 7 hereinafter.

The process of the present invention can be performed on a commercial scale with reduced expenditures for apparatus, for example, by eliminating the necessity for resolving, cleaving, and recovering the resolving agents after each separation before racemization, as well as expenditures for power. Further savings are realized by elimination of the requirement for purifying the pantolactone, and eliminating the costs of procuring the resolving agents, and losses resulting from their use, and further savings in operating time, which is made possible by the simplification achieved by the process of the present invention. By elimination of the requirement for the use of toxic substances, the working conditions and environment have also been improved.

DETAILED DESCRIPTION AND PREFERRED EMBODIMENTS

The processes of the present invention are further described and illustrated by the examples which follow.

EXAMPLE 1. Preparation of DL-lithium pantoate monohydrate.

A slurry of 1.00 kilogram of racemic DL-pantolactone and 300 grams of lithium carbonate in 1.5 liters of water was continuously stirred and heated at boiling temperature in a flask provided with a stirrer and reflux condenser for 1.5 hours. After all the evolved carbon dioxide had been expelled, the reaction mixture was filtered while hot and 25 grams of lithium carbonate was thus recovered therefrom. When the filtrate was cooled and stirred, 700 grams of crystals of racemic DL-lithium pantoate monohydrate having a melting point of 107°–110° C. amounting to 53.0% of the theoretical yield, separated and was collected. By evaporation of the mother liquor a further amount of DL-lithium pantoate, equivalent to 42% of the original DL-pantolactone, was recovered.

EXAMPLE 2. Preparation of anhydrous DL-lithium pantoate.

A slurry of 1.0 kilogram of DL-pantolactone (racemic) and 340 grams of lithium hydroxide monohydrate in 2.50 liters of methanol was heated at boiling temperature with continuous stirring for 2.5 hours in the apparatus that was described in Example 1. Carbon dioxide was thereafter injected into the reaction mixture and its hydrogen-ion concentration was brought to a value corresponding to a pH of 7.5. The lithium carbonate that was thus formed was then separated from the hot reaction mixture by filtration. After cooling, 620 grams of crystals of DL-lithium pantoate, having a melting point of 180°-182° C, were recovered from the filtrate, which amount is equivalent to 50% of the theoretical yield.

By evaporation of the mother liquor, DL-lithium pantoate monohydrate having a melting point of 107°-110° C, equivalent to 43% of the original pantolactone, was recovered.

EXAMPLE 3. Preparation of DL-lithium pantoate monohydrate.

A slurry of 334 grams of DL-calcium pantoate and 102 grams of lithium oxalate in 600 grams of water was heated at boiling temperature with continuous stirring in the apparatus described in Example 1 for 4 hours. The resulting mixture was then filtered while hot and the calcium oxalate that was thus separated was washed three times with 70-milliliter portions of hot water. The filtrate and wash waters were then combined and evaporated in a rotary vacuum evaporator to a volume of 400 milliliters during which 254 grams of DL-lithium pantoate monohydrate having a melting point of 107°-110° C, equivalent to 74% of the theoretical yield, separated and was collected. From the mother liquor by further concentration, DL-lithium pantoate monohydrate, in an amount equivalent to 20% of the original DL-pantolactone, was recovered.

EXAMPLE 4. Preparation of DL-lithium pantoate monohydrate.

A slurry of 431 grams of barium pantoate and 128 grams of lithium sulfate monohydrate in 1000 milliliters of water was heated at boiling temperature with continuous stirring for 6 hours in the apparatus described in Example 1 hereinbefore. Barium sulfate which formed in the reaction mixture was separated by filtration from the hot mixture and washed with three 80-milliliter portions of hot water. The filtrate and wash water were then combined and evaporated in a rotary vacuum evaporator as described in Example 3 and the DL-lithium pantoate recovered as therein described. A total of 320 grams of DL-lithium pantoate monohydrate having a melting point of 107°-110° C, equivalent to 93% of the theoretical yield, was thus obtained.

EXAMPLE 5. Separation of D-lithium pantoate from DL-lithium pantoate

To a solution of 50 grams of DL-lithium pantoate and 10 grams of D-lithium pantoate in 110 milliliters of methanol that was prepared by heating the mixture to a temperature of 60° C was added 0.1 gram of seed crystals of D-lithium pantoate. After stirring for 60 minutes and subsequently letting the seeded mixture stand for 3 hours, the crystals that formed in the solution were separated by filtration and dried. There was thus obtained 19 grams of D-lithium pantoate having an optical purity of 98% whose specific optical rotation $[\alpha]_D^{20}$ (c - 10.0) was 10.0°. (The symbol "c - 10.0" refers to a solution of 1 gram of the substance in 10 milliliters of water).

EXAMPLE 6. Separation of L-lithium pantoate from DL-lithium pantoate

A solution of 100 grams of DL-lithium pantoate and 8 grams of L-lithium pantoate in 1.1 liters of ethanol that was prepared by heating the mixture to a temperature of 62° C was inoculated with several seed crystals of L-lithium pantoate and cooled to a temperature of 2° C with continuous stirring and then permitted to stand undisturbed for 3 days at 2° C. The crystals thus formed in the solution were separated by filtration, washed successively with 10 milliters of ethanol and 5 milliliters of acetone and dried. In this manner was obtained 17 grams of L-lithium pantoate crystals having an optical purity of 87%, whose specific optical rotation $[\alpha]_D^{20}$ (c - 10.0) was 9.0°.

EXAMPLE 7. Resolution of DL-lithium pantoate into D(+)-lithium pantoate and L(−)-lithium pantoate A solution of 895 grams of DL-lithium pantothenate in 1800 milliliters of methanol was prepared by stirring and warming the mixture to a temperature of 65° C. Subsequently this saturated solution was seeded with 1 gram of a mixture of crystals of pure D(+)-lithium pantoate and L(−)-lithium pantoate and the solution was cooled gradually to a temperature of 20° C at the rate of 0.33 centigrade degree per minute while it was stirred continuously. The crystals that thus formed in the solution were then separated by suction filtration and dried in the air, being continuously stirred during the drying period.

The dried crystalline material thus obtained, which consists of a racemic mixture of D-lithium pantoate and L-lithium pantoate was then subjected to separation in a free-fall separator comprising two metallic plate electrodes between which an electrostatic field having a electrical potential of 6 kilovolts per centimeter was maintained. In this manner, two fractions, each having an optical purity of 69%, were obtained.

To dissolve out the portions of racemic DL-lithium pantoate that each of these fractions contained, each fraction was stirred for 180 minutes with 1200 milliliters of methanol at a temperature of 25° C and subsequently cooled to a temperature of 10° C and stirred for an additional period of 60 minutes. The crystals were then separated from the methanol by suction filtration and dried. In this manner, 102 grams of pure D(+)-lithium pantoate and 108 grams of pure L(−)-lithium pantoate were obtained. The L(−)-lithium pantoate was subsequently subjected to racemization as described in Example 9 hereinafter.

The racemic DL-lithium pantoate that remained in solution in the methanol was crystallized therefrom by adding thereto a seed crystal of a racemic mixture of D-lithium pantoate and L-lithium pantoate.

EXAMPLE 8. Racemization of L(−)-lithium pantoate

To a solution of 57 grams of L(−)-lithium pantoate having a specific optical rotation $[\alpha]_D^{20}$ of −10.2° (c - 10.0) in 500 milliliters of methanol that was contained in a 1-liter autoclave was added 5 milliliters of diethylamine and the mixture was heated at a temperature of 160° C under its own autogenous pressure, which was a superatmospheric pressure of 17 atmospheres.

After cooling, the diethylamine was separated by distillation. Methanol was then added to the residue to form a suspension of DL-lithium pantoate crystals. In this manner 54 grams of DL-lithium pantoate, equivalent to 94.6% of the theoretical yield, was obtained by racemization of the L(−)-lithium pantoate. The D-lithium pantoate was separated from the DL-lithium pantoate thus obtained in accordance with the process described in Example 5 hereinbefore.

EXAMPLE 9. Racemization of L(−)-lithium pantoate

To a solution of 100 grams of L(−)-lithium pantoate in 500 milliliters of methanol that was contained in a 1-liter autoclave was added 13.5 grams of lithium hydroxide monohydrate and the mixture was heated for 2.5 hours at a temperature of 160° C under its own autogenous pressure, which was a superatmospheric pressure of 17 atmospheres. The mixture was cooled and carbon dioxide was then passed into the mixture until the liquid portion of the mixture had a hydrogen-ion concentration corresponding to a pH of 7.5. The lithium carbonate that was thus formed was separated by filtration and the filtrate was evaporated to a concentration required for use in separation of the D-lithium pantoate from the resulting racemic mixture in accordance with the process described in Example 5 hereinbefore. The amount of DL-lithium pantoate that was thus obtained from the L(−)-lithium pantoate in this example was equivalent to 95% of the theoretical yield.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention.

What is claimed as new and described to be protected by Letters Patent is set forth in the appended claims.

1. Optically active D-lithium pantoate.
2. The process for obtaining the compound of claim 1 in separate form the said process comprising
    (a) forming a supersaturated solution of DL-lithium pantoate in a polar solvent;
    (b) subjecting the solution to crystallizing conditions while seeding it with crystals
        (a) of D-lithium pantoate so as to cause selective crystallization of the D-lithium pantoate from the solution, or
        (b) seeding the solution with both types of enantiomorphs of lithium pantoate followed by crystallization to obtain a racemic mixture of D-lithium pantoate and L-lithium pantoate and thereafter separating the mixture in in an electrostatic separator into two fractions of predominantly D(+) and L(−) lithium pantoate after dissolving out residual fractions of DL-lithium pantoate, and
    (c) finally recovering the D-lithium pantoate by separating it from the L-lithium pantoate.
3. The process of claim 2, wherein the obtained L-lithium pantoate is re-racemized and the thus formed D,L-lithium pantoate is recycled into the DL-lithium pantoate as starting compound.
4. The process of claim 3 wherein the re-racemization is effected by heating the L-lithium pantoate in form of a solution in a polar solvent to a temperature between 120° and 180° C in the presence of an alkaline catalyst.

* * * * *